US007298813B2

(12) United States Patent
Tsuyuki et al.

(10) Patent No.: US 7,298,813 B2
(45) Date of Patent: Nov. 20, 2007

(54) X-RAY COMPUTED TOMOGRAPHIC APPARATUS, IMAGE PROCESSING APPARATUS, AND IMAGE PROCESSING METHOD

(75) Inventors: Masaharu Tsuyuki, Nasushiobara (JP); Satoru Nakanishi, Utsunomiya (JP); Satoshi Saito, Yaita (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 11/367,461

(22) Filed: Mar. 6, 2006

(65) Prior Publication Data
US 2006/0198490 A1 Sep. 7, 2006

(30) Foreign Application Priority Data
Mar. 7, 2005 (JP) .............................. 2005-062645

(51) Int. Cl.
*A61B 6/03* (2006.01)
(52) U.S. Cl. ........................................... 378/8; 378/15
(58) Field of Classification Search .................. 378/8, 378/4, 15, 901, 20
See application file for complete search history.

(56) References Cited

U.S. PATENT DOCUMENTS

| 6,466,640 | B1 | 10/2002 | Taguchi | |
|---|---|---|---|---|
| 6,526,117 | B1 * | 2/2003 | Okerlund et al. | 378/8 |
| 7,127,025 | B2 * | 10/2006 | Bruder et al. | 378/8 |
| 2003/0002616 | A1 * | 1/2003 | Cesmeli | 378/8 |
| 2006/0198491 | A1 * | 9/2006 | Taguchi | 378/15 |

FOREIGN PATENT DOCUMENTS

JP 2001-149365 6/2001

* cited by examiner

*Primary Examiner*—Hoon Song
(74) *Attorney, Agent, or Firm*—Oblon, Spivak, McClelland, Maier & Neustadt, P.C.

(57) ABSTRACT

An X-ray computed tomographic apparatus includes a gantry unit having a detector having X-ray detection element rows along a slice direction and an X-ray tube and acquiring projection data from a subject by helical scanning, an extraction unit extracting first and second projection data sets corresponding to first and second heartbeat periods from the acquired projection data, each of the first and second projection data sets covering an angle range required for the reconstruction of one frame image, a processing unit weighting each of the extracted first and second projection data sets with a weight corresponding to a data acquisition position and generating a third data set by combining the weighted first and second projection data sets, and a reconstruction processing unit reconstructing one frame image data set on the basis of the generated third data set.

18 Claims, 10 Drawing Sheets

X-RAY COMPUTED TOMOGRAPHIC APPARATUS, IMAGE PROCESSING APPARATUS, AND IMAGE PROCESSING METHOD

CROSS-REFERENCE TO RELATED APPLICATIONS

This application is based upon and claims the benefit of priority from prior Japanese Patent Application No. 2005-062645, filed on Mar. 7, 2005, the entire contents of which are incorporated herein by reference.

BACKGROUND OF THE INVENTION

1. Field of the Invention

The present invention relates to an X-ray computed tomographic apparatus which scans a subject by helical scanning, and reconstructs image data in an ECG-gated reconstruction method on the basis of the obtained data.

2. Description of the Related Art

An X-ray computed tomographic apparatus provides information concerning a subject in the form of images on the basis of the intensities of X-rays transmitted through the subject, and plays an important role in many medical activities including diagnoses and medical treatments for diseases, surgical planning, and the like.

It is an important challenge to improve the time resolution of images in examinations on subjects with fast movement, especially in cardiac examinations, which use X-ray computed tomographic apparatuses. A main method for this challenge is a combination of a half reconstruction method and an ECG-gated reconstruction method. As is known, image data is reconstructed by a projection data set acquired while an X-ray tube rotates in the range of $180°+\alpha$ (where $\alpha$ is the fan angle) centered on the phase of the movement of the heart which is designated by an operator. Recently, attempts have been made to apply a half ECG-gated reconstruction method to helical scanning operation using a detector corresponding to multislice operation (multi-row detector).

FIG. 10 shows a data existing range (the paths of the respective detector rows) together with an electrocardiogram (ECG), with the abscissa representing time and the ordinate representing the position on the Z-axis (body axis). Data sets in the $180°+\alpha$ ranges (thick lines) centered on designated phases on slices Z1 and Z2 are generated by helical interpolation, and tomographic images are reconstructed from the generated data sets. Likewise, tomographic images of a plurality of slices are reconstructed at predetermined intervals. In an actual examination, by using tomographic images of a plurality of slices, an image of a section in an arbitrary direction crossing them is generated by MPR (Multi-Planar Reformatting).

For example, an image of the slice Z1 originates from a data set at a second heartbeat 2, and an image of the adjacent slice Z2 originates from a data set at a third heartbeat 3. Since an MPR image is generated by partially combining images in different heartbeat periods, banding artifacts (a plurality of discontinuities in an image) are produced in an MPR image due to body movement such as respirations during heartbeat periods, as exemplified by FIG. 7A.

BRIEF SUMMARY OF THE INVENTION

It is an object of the present invention to reduce banding artifacts in an X-ray computed tomographic apparatus, image processing apparatus, and image processing method which scan a subject by helical scanning, and reconstruct image data in an ECG-gated reconstruction method on the basis of obtained data.

According to a first aspect of the present invention, there is provided an X-ray computed tomographic apparatus comprising a gantry unit which includes a detector with a plurality of X-ray detection element rows along a slice direction and an X-ray tube and acquires projection data from a subject by helical scanning, an extraction unit which extracts a first projection data set corresponding to a first heartbeat period or a first respiratory period of the subject and a second projection data set corresponding to a second heartbeat period or a second respiratory period of the subject from the acquired projection data, each of the first projection data set and the second projection data set covering an angle range required for reconstruction of a 1-frame image, a weighting processing unit which weights each of the extracted first projection data set and the extracted second projection data set with a weight corresponding to a data acquisition position, a combining processing unit which generates a third data set by combining the weighted first projection data and the weighted second projection data, and a reconstruction processing unit which reconstructs a 1-frame image data set on the basis of the generated third data set.

According to a second aspect of the present invention, there is provided an X-ray computed tomographic apparatus comprising a gantry unit which includes a detector with a plurality of X-ray detection element rows along a slice direction and an X-ray tube and acquires projection data from a subject by helical scanning, an extraction unit which extracts a first projection data set corresponding to a first heartbeat period or a first respiratory period of the subject and a second projection data set corresponding to a second heartbeat period or a second respiratory period of the subject from the acquired projection data, each of the first projection data set and the second projection data set covering an angle range required for reconstruction of a 1-frame image, a weighting processing unit which weights each of the extracted first projection data set and the extracted second projection data set with a weight corresponding to a data acquisition position, a reconstruction processing unit which reconstructs a first image data set and a second image data set on the basis of the weighted first projection data set and the weighted second projection data set, and a combining processing unit which generates a third image data set by combining the reconstructed first image set and the reconstructed second image data set.

According to a third aspect of the present invention, there is provided an X-ray computed tomographic apparatus comprising a gantry unit which includes a detector with a plurality of X-ray detection element rows along a slice direction and an X-ray tube and acquires projection data from a subject by helical scanning, an extraction unit which extracts a first projection data set corresponding to a first heartbeat period or a first respiratory period of the subject and a second projection data set corresponding to a second heartbeat period or a second respiratory period of the subject from the acquired projection data, each of the first projection data set and the second projection data set covering an angle range required for reconstruction of a 1-frame image, a reconstruction processing unit which reconstructs a first image data set and a second image data set on the basis of the extracted first projection data set and the extracted second projection data set, a weighting processing unit which weights each of the reconstructed first image data set and the reconstructed second image data set with a weight corresponding to a data acquisition position, and a combining processing unit which generates third image data by combining the weighted first image data set and the weighted second image data set.

According to a fourth aspect of the present invention, there is provided an X-ray computed tomographic apparatus comprising a gantry unit which includes a detector with a plurality of X-ray detection element rows along a slice direction and an X-ray tube and acquires projection data from a subject by helical scanning, an extraction unit which extracts a plurality of projection data sets in different heartbeat periods or respiratory periods of the subject from the acquired projection data, each of the projection data sets covering an angle range required for reconstruction of a 1-frame image, and a reconstruction processing unit which reconstructs a 1-frame image data set possessing a weight corresponding to a data acquisition position of each of the projection data sets on the basis of the plurality of extracted projection data sets.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

An X-ray computed tomographic apparatus according to an embodiment of the present invention will be described with reference to the several views of the accompanying drawing. Note that X-ray computed tomographic apparatuses include various types of apparatuses, e.g., a rotate/rotate-type apparatus in which an X-ray tube and X-ray detector rotate together around a subject, and a stationary/rotate-type apparatus in which many detection elements are arrayed in the form of a ring, and only an X-ray tube rotates around a subject. The present invention can be applied to either type. In this case, the rotate/rotate type, which is currently the mainstream, will be exemplified. In order to reconstruct 1-slice tomographic image data, about 360° projection data corresponding to one rotation around a subject is required, or 180°+α (where α is a fan angle) projection data is required in the half scan method. This embodiment uses the half scan method which is effective in imaging the heart and the like with fast movement. As mechanisms of converting incident X-rays into electric charges, the following techniques are the mainstream: an indirect conversion type that converts X-rays into light through a phosphor such as a scintillator and converts the light into electric charges through photoelectric conversion elements such as photodiodes, and a direct conversion type that uses generation of electron-hole pairs in a semiconductor by X-rays and movement of the electron-hole pairs to an electrode, i.e., a photoconductive phenomenon. As an X-ray detection element, either of these schemes can be used. In this case, the former type, i.e., the indirect conversion type, will be exemplified. Recently, with advances toward the commercialization of a so-called multi-tube type X-ray computed tomographic apparatus having a plurality of pairs of X-ray tubes and X-ray detectors mounted on a rotating ring, related techniques have been developed. The present invention can be applied to both a conventional single-tube type X-ray computed tomographic apparatus and a multi-tube type X-ray computed tomographic apparatus. In this case, the single-tube type X-ray computed tomographic apparatus will be exemplified here.

Figure 1:
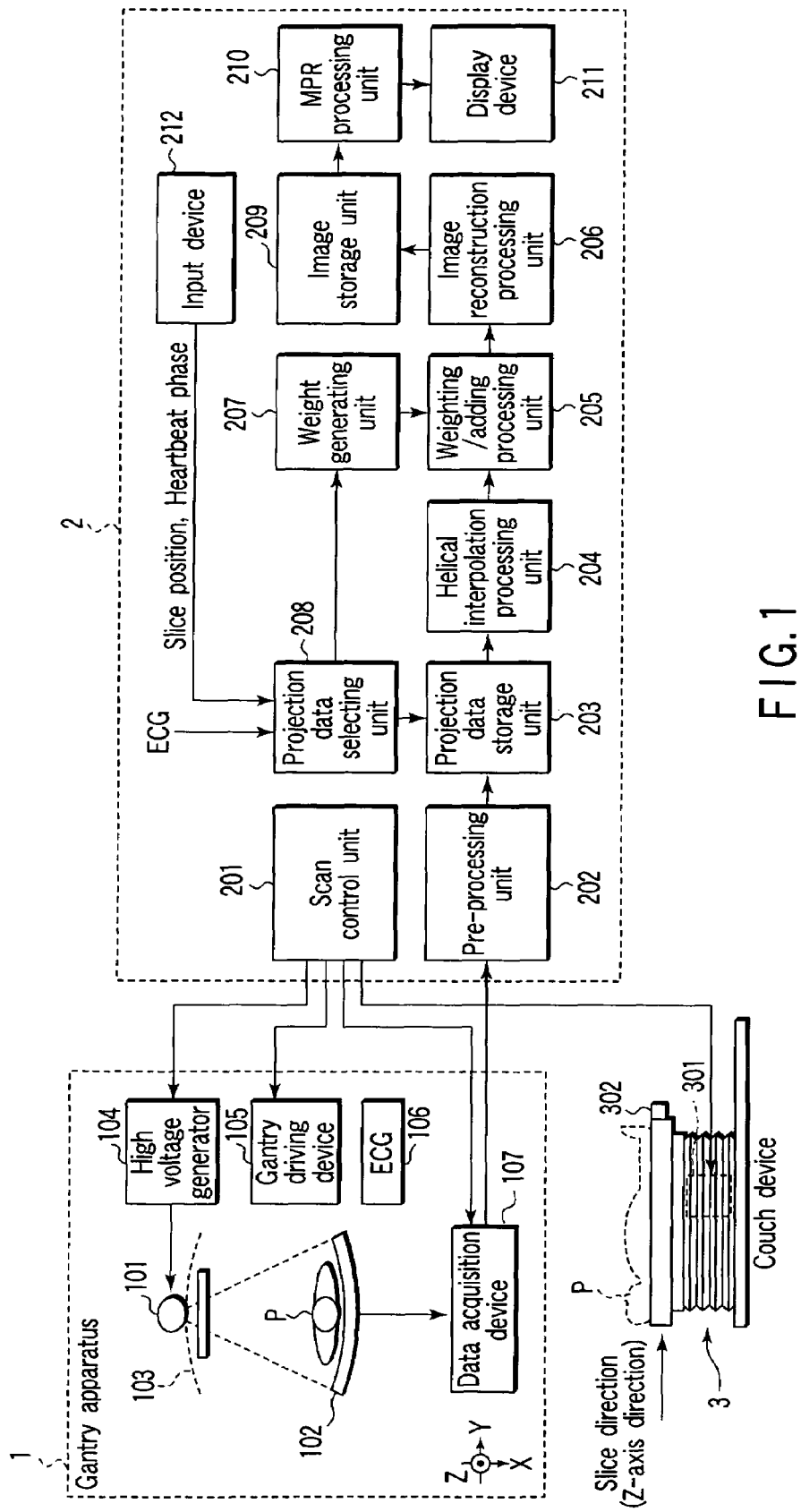
FIG. 1 is a block diagram showing the arrangement of an X-ray computed tomographic apparatus according to an embodiment of the present invention.

FIG. 1 shows the arrangement of an X-ray computed tomographic apparatus according to this embodiment. This X-ray computed tomographic apparatus has a gantry apparatus 1 configured to acquire projection data concerning a subject. The gantry apparatus 1 has an X-ray tube 101 and a multislice type X-ray detector 102. The X-ray tube 101 and the X-ray detector 102 are mounted on a ring-like rotating frame 103 which is rotated/driven by a gantry driving device 105. The rotation axis of the rotating frame 103 is defined as the Z-axis. In this case, a rotary coordinate system centered on the Z-axis is specified. An axis perpendicular to the Z-axis connecting the focal point of the X-ray tube 101 and the center of the detection surface of the X-ray detector 102 is defined as the X-axis. The Y-axis is perpendicular to both the Z-axis and the X-axis.

An opening portion is formed in the central portion of the rotating frame 103. A subject P placed on a top 302 of a bed device 3 is inserted in the opening portion. In order to detect an electrocardiogram of the subject P, an electrocardiograph 106 is mounted on the subject P. Note that the electrocardiograph 106 is mounted as a device for measuring a biometric signal of the subject P. This device may be a respirometer which measures the periodical respiratory movement of the subject P.

A high voltage generator 104 applies a tube voltage (high voltage) between the cathode and anode of the X-ray tube 101. In addition, the high voltage generator 104 supplies a filament current to the filament of the X-ray tube 101. X-rays are generated by applying a tube voltage and supplying a filament current to the X-ray tube 101.

The multislice type X-ray detector 102 has a plurality of X-ray detection elements each having, for example, a 0.5 mm×0.5 mm square light-receiving surface. For example, 916 X-ray detection elements are arrayed in a channel direction (approximate to the Y-axis). For example, 40 such rows are arranged side by side in a slice direction (Z-axis). The X-ray detector 102 may be a so-called two-dimensional array type X-ray detector having a plurality of X-ray detection elements arranged in the form of a matrix along the X- and Y-axes.

A data acquisition device 107 generally called a DAS (Data Acquisition System) converts a signal output from the X-ray detector 102 for each channel into a voltage signal, amplifies it, and converts it into a digital signal. This data (also called raw data) is supplied to a computer main body 2 outside the gantry. A pre-processing unit 202 of the computer main body 2 performs correction processing such as sensitivity correction for the data (raw data) output from the data acquisition device 107. The pre-processed raw data is generally called projection data. The projection data is stored in a projection data storage unit 203 of the computer main body 2, together with the electrocardiogram data from the electrocardiograph 106, in association with codes representing a view angle representing the rotational angle of the X-ray tube 101, a channel number, a row number, and the position of the top 302.

In addition to the pre-processing unit 202 and the projection data storage unit 203, the computer main body 2 has a scan control unit 201, helical interpolation processing unit 204, weighting/adding processing unit 205, image reconstruction processing unit 206, weight generating unit 207, projection data selecting unit 208, image storage unit 209, MPR processing unit (Multi-Planar Reformatting) 210, display device 211, and input device 212. The projection data selecting unit 208 performs read control for the projection data storage unit 203 with respect to at least projection data in an angle range necessary for half reconstruction which corresponds to a slice (a position on the Z-axis) designated from the input device 212 and a heartbeat phase designated from the input device 212, i.e., projection data corresponding to the angle range of 180°+fan angle α in this embodiment.

The helical interpolation processing unit 204 generates a plurality of data sets at the same slice position in different heartbeat periods by performing distance interpolation, centered on a slice designated from the input device 212, for data in the angle range of 180°+fan angle α centered on a heartbeat phase (specific phase) designated from the input device 212 (data corresponding to the angle range of 180°+fan angle α will be simply referred to as a data set hereinafter). One data set covers the angle range (180°+fan angle α) required for the reconstruction of 1-frame image data.

A single or a plurality of slices may be designated. However, multislice helical scanning is often directed to generate volume data or MPR images (multi-planar reformatted images). Typically, many slices are often designated at once with reconstruction ranges extending in the Z-axis direction (which are called D-FOVs in distinction from scan ranges S-FOVs) and slice intervals.

Distance interpolation using the helical interpolation processing unit 204 is a general technique, in which projection data at different Z positions, typically two different Z-positions, on both sides of a designated slice are weighted and added in accordance with the distances from the designated slice. Repeating this processing for each of a plurality of view angles within the angle range of 180°+fan angle α makes it possible to prepare data sets concerning the designated slice described above. In this embodiment, a plurality of data sets in different heartbeat periods are generated for each slice.

The weighting/adding processing unit 205 generates a single data set for each slice by weighting/adding a plurality of data sets concerning the same slice in different heartbeat periods, which are generated by the helical interpolation processing unit 204, by using weights determined for the respective data sets and generated by the weight generating unit 207. Reconstructed tomographic image data concerning a plurality of slices are stored in the image storage unit 209, together with codes representing the respective slice positions. The MPR processing unit 210 generates volume data as a voxel aggregate from tomographic image data concerning a plurality of slices by performing interpolation between the slices using an arbitrary technique. The MPR processing unit 210 also generates tomographic image data concerning a designated slice in an arbitrary direction from volume data. The generated tomographic image data is displayed on the display device 211.

Figure 2A:
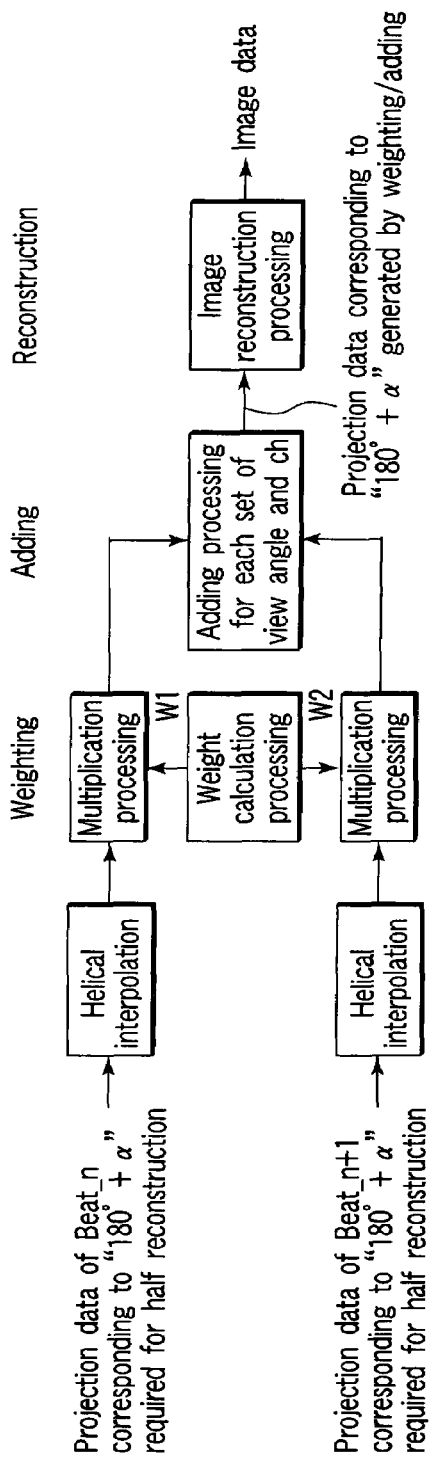
FIGS. 2A and 2B are views showing an outline of the flow of image reconstruction processing for one slice according to this embodiment.
Figure 3:
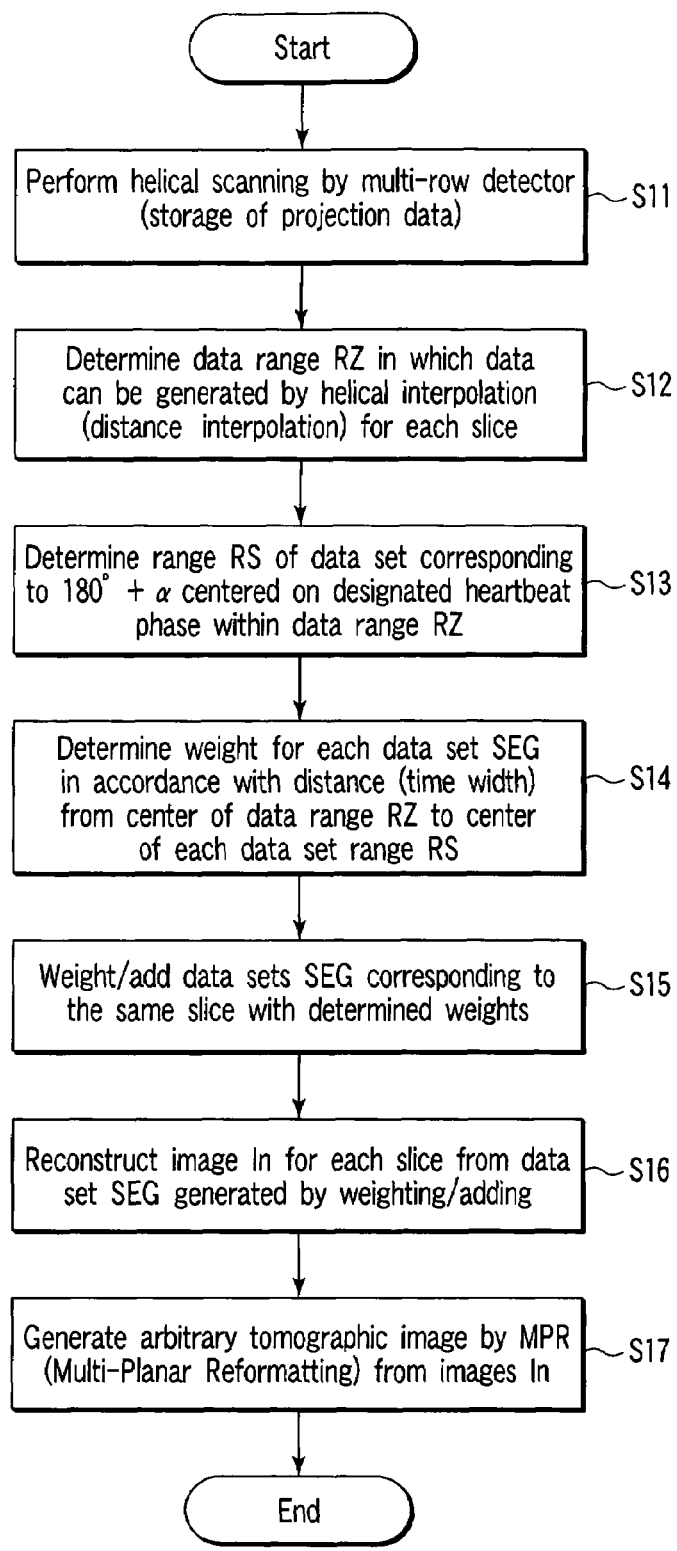
FIG. 3 is a flowchart showing the flow of processing from helical scanning (data acquisition) to the generation of an MPR image according to this embodiment.
Figure 4:
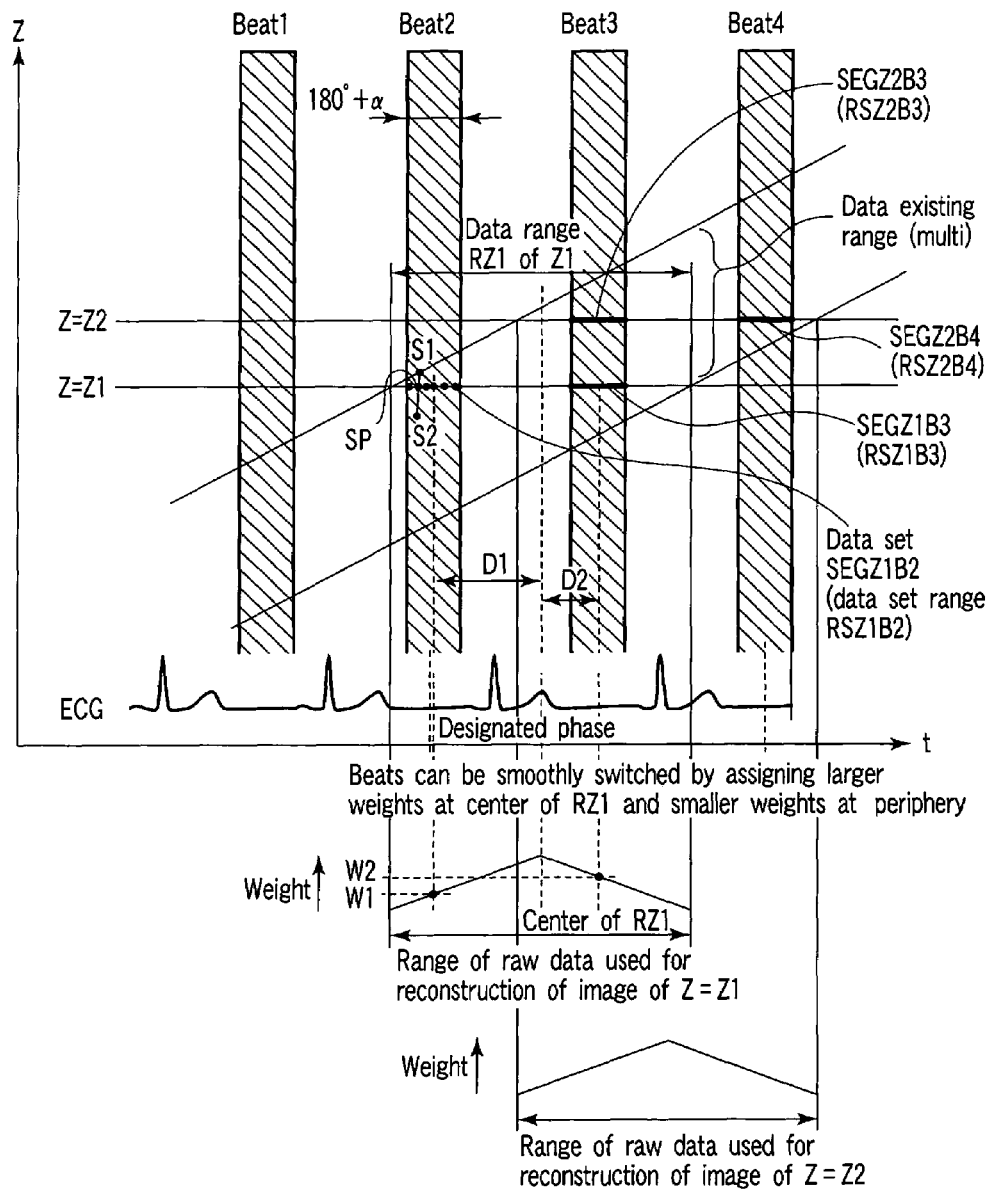
FIG. 4 is a view for supplementarily explaining a weight determination method in S14 in FIG. 3.

FIG. 2A shows an outline of the flow of image reconstruction processing for one slice corresponding to a fan beam in this embodiment. FIG. 3 shows the overall flow of processing between helical scanning (data acquisition) and the generation of an MPR image in this embodiment. Image reconstruction processing in this embodiment will be described with reference to FIG. 4. FIG. 4 shows a data existing range (the paths of the respective detector rows) extending obliquely, together with an electrocardiogram (ECG), with the abscissa representing time and the ordinate representing the position on the Z-axis (body axis). Referring to FIG. 4, the band (to be referred to as the designated phase band) of the angle range of 180°+fan angle α centered on a heartbeat phase (specific phase) designated from the input device 212 is indicated by the oblique lines.

First of all, helical scanning is executed with a designated helical pitch throughout a designated range by using the multiple rows of the X-ray detector 102 (S11). When the helical scanning operation is complete, the acquired projection data are stored in the projection data storage unit 203. The projection data selecting unit 208 then specifies a range RZ1 in which a slice Z1 crosses the data existing range (S12). The range RZ1 represents a range in which projection data on the slice Z1 can be prepared by helical interpolation (interpolation). At least two ranges RS(Z1B2) and RS(Z1B3) which fall within this data existing range and in which the designated slice Z1 crosses at least two adjacent designated phase bands in different heartbeat periods are determined (S13). Note that a helical pitch as a distance that the top 302 moves within the time required for one rotation of the rotating frame 103 is properly set in advance such that a designated slice crosses designated phase bands in at least two adjacent heartbeat periods which fall within the data existing range.

The projection data selecting unit 208 further specifies two positions S1 and S2 on detector row paths which are nearest to each other and located on both sides of the designated slice Z1 for each of discrete sampling points SP on the respective data set ranges RS(Z1B2) and RS(Z1B3). The helical interpolation processing unit 204 weights/adds specified projection data in accordance with the distances from the slice Z1. This helical interpolation processing is repeated for each of a plurality of sampling points SP in the angle ranges RS(Z1B2) and RS(Z1B3) of 180°+fan angle α, i.e., each of view point on the rotation path of the focal point of the X-ray tube which are interspaced from each other at intervals of 2° or the like, thereby preparing two data sets SEG(Z1B2) and SEG(Z1B3) concerning the slice Z1.

The weight generating unit 207 determines weights for the two data sets SEG(Z1B2) and ZEG(Z1B3) concerning the slice Z1 in different heartbeat periods (S14). Weights are determined for the respective data sets SEG(Z1B2) and SEG(Z1B3) in accordance with distances (time widths) D1 and S2 from the center of the range RZ1 in which the slice Z1 crosses the data existing range to the centers of the respective angle ranges RS(Z1B2) and RS(Z1B3).

Figure 5:
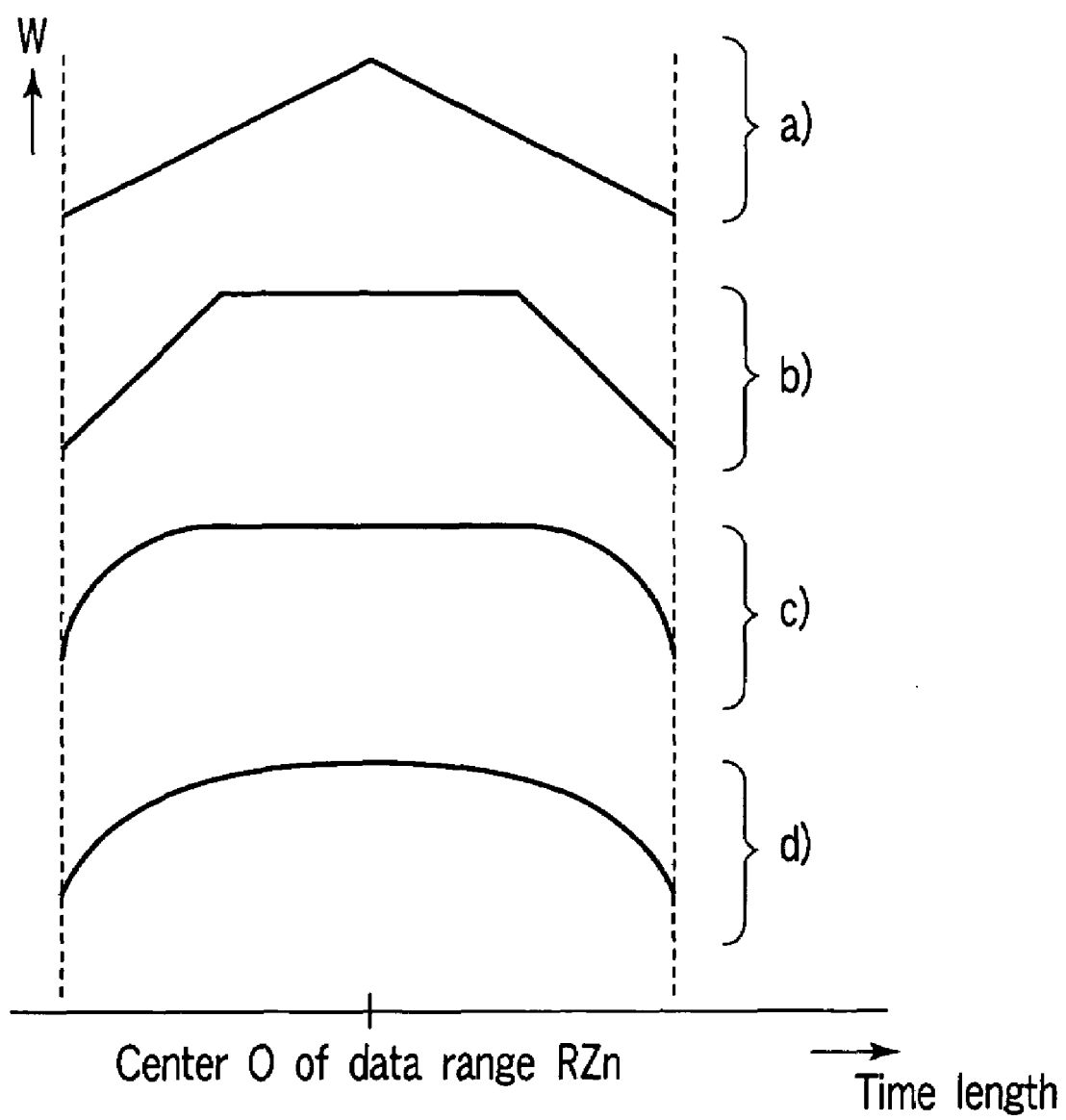
FIG. 5 is a graph showing variations of weighting functions generated by a weight generating unit in FIG. 1.
Figure 6:
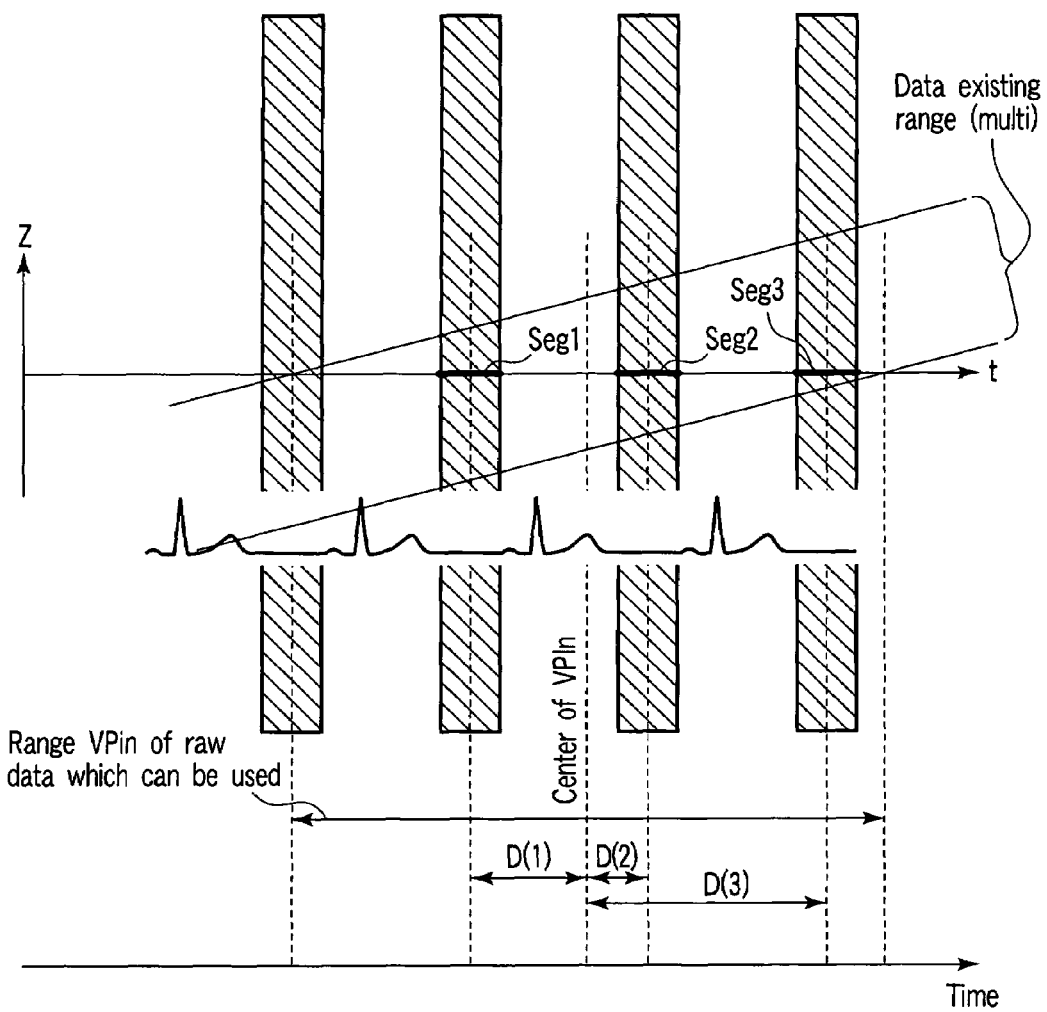
FIG. 6 is a view for supplementarily explaining another weight determination method in S14 in FIG. 3.

Weights are determined in accordance with intervals D1 and D2 from the center of the range RZ1 in which the data sets SEG(Z1B2) and SEG(Z1B3) concerning the slice position Z1 in the angle range of 180°+fan angle can be prepared by helical interpolation to the centers of the angle ranges RS(Z1B2) and RS(Z1B3) of the respective data set. As shown in FIG. 4, as the center of each of the angle ranges RS(Z1B2) and RS(Z1B3) of the respective data sets approaches the center of the range R1, i.e., the distance D decreases, a weight is determined such that its value becomes higher, i.e., the value becomes nearer to "1" in this case. There are various concrete methods of determining weights. For example, as shown in FIG. 5A, the value of a weight is determined by a linear function that linearly decreases from the center of a range RZ in which a data set in an angle range RS of 180°+fan angle which concerns a designated slice can be prepared from data by interpolation to an end of the range. Alternatively, as shown in FIG. 5B, the value of a weight is determined such that the value approximately changes in a trapezoidal shape from the center of the range RZ in which a data set in the angle range RS of 180°+fan angle which concerns a designated slice can be prepared from data by interpolation to an end of the range. Alternatively, as shown in FIGS. 5C and 5D, the values of weights are determined by various kinds of curve functions that gradually decrease in the form of curves from the center of the range RZ in which a data set in the angle range RS of 180°+fan angle which concerns a designated slice can be prepared from data by interpolation to an end of the range.

Weights may also be determined in the following manner. According to the above description, a weight is determined in accordance with the distance (time width) D from the center of the range RZ in which a designated slice crosses the data existing range to the center of the angle range RS. As indicated by equation (1) below, however, as the value obtained by subtracting the absolute value of the distance (time width) D from ½ of a width VP1 of the range RZ in which a designated slice crosses the data existing range, i.e., the distance from an end of the range RZ, increases, a weight may be determined such that its value becomes higher, i.e., the value becomes nearer to "1" in this case. According to equation (1), weights are normalized such that the total of the weights with respect to the respective data sets becomes 1. Determining a weight in accordance with the distance from an end of the range in this manner makes it possible to cope with a specific situation in which the center of the data set range RS coincides with the center of the range RZ. In this specific situation, according to the weight determination method shown in FIG. 4, the distance D becomes zero, and hence weights may diverge.

A weight W(i) for SEGi is expressed by $$w(i) = \frac{0.5 \cdot VPIn - |D(i)|}{\sum_{i=1}^{i=Npatch} (0.5 \cdot VPI - |D(i)|)} \quad (1)$$

When weights are determined, the weighting/adding processing unit 205 weights/adds a plurality of data sets concerning the same slice in different heartbeat periods, e.g., a data set SEG(Z1B2) concerning the slice Z1 in a second heartbeat period Beat 2 and a data set SEG(Z1B3) concerning the same slice Z1 in a third heartbeat period Beat 3, for each view angle and channel, by using weights W1 and W2 (S15). With this operation, a single data set SEG(Z1) concerning the slice Z1 crossing a plurality of heartbeat periods is generated. With respect to other slices Z2, . . . , data sets SEG(Z2), . . . are generated in the same manner as described above.

The image reconstruction processing unit 206 reconstructs a plurality of tomographic images (data) I(Z1), I(Z2), . . . concerning a plurality of consecutive slices from a plurality of data sets SEG(Z1), SEG(Z2), . . . concerting the plurality of slices (S16). The plurality of tomographic image data I(Z1), I(Z2), . . . concerning the plurality of slices are stored in the image storage unit 209. When an instruction to generate an image of an arbitrary oblique cross-section which tilts with respect to the Z-axis (multi-planar reformatting processing) is issued through the input device 212, data at positions (pixels) approximating the designated cross-section are selectively read out from the image storage unit 209 to the MPR processing unit 210. The MPR processing unit 210 generates the data of the pixels on the cross-section by interpolating the readout data (S17). The generated image of the arbitrary cross-section is displayed on the display device 211.

Figure 7A:
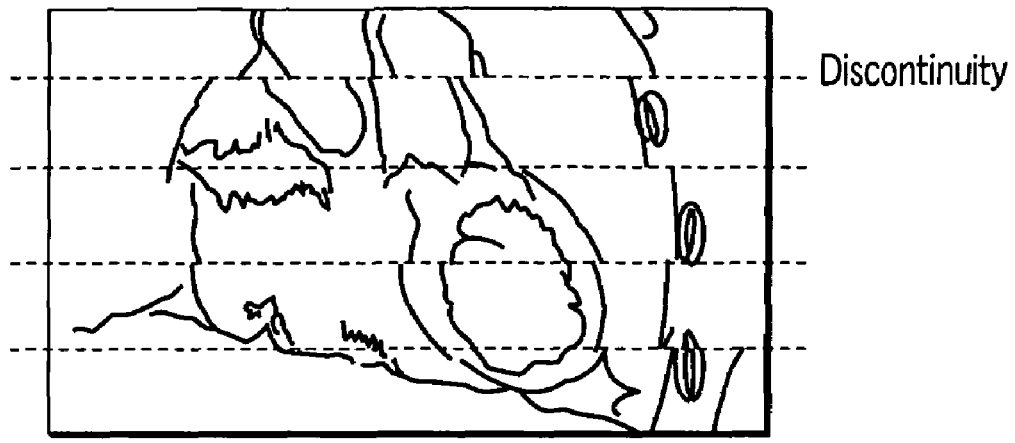
FIGS. 7A and 7B are views each showing an example of an MPR image according to this embodiment.
Figure 7B:
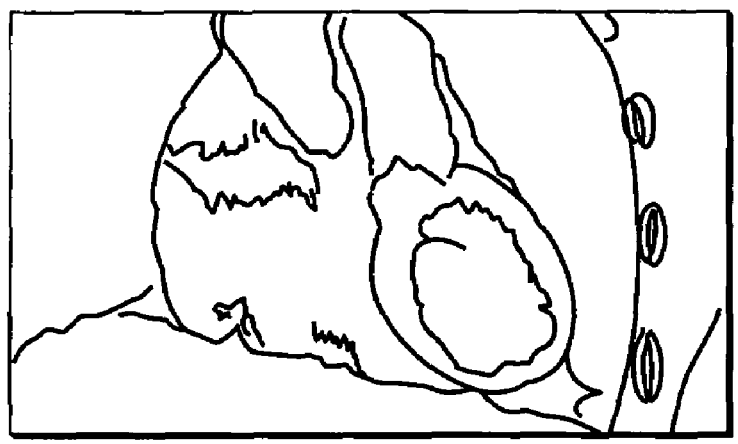

As has been described above, according to this embodiment, since a tomographic image of each slice is generated from data acquired in a plurality of heartbeat periods, the occurrence of banding artifacts (steps in an image) like those shown in FIG. 7A due to body movement such as respirations during heartbeat periods is reduced (see FIG. 7B).

Figure 2B:
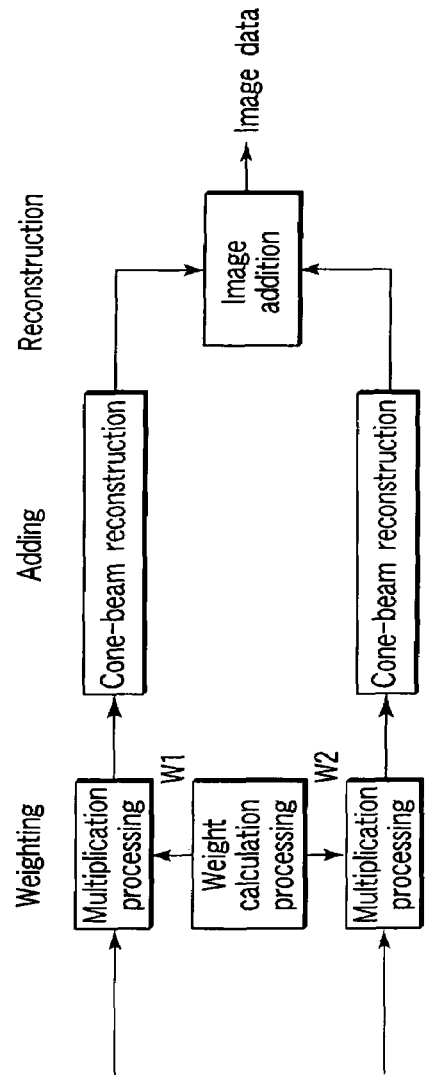

The above description has been made about the flow of image reconstruction processing corresponding to a fan beam. However, when projection data is to be acquired by performing helical scanning using a so-called cone-beam CT scanner which generates X-rays in the form of a cone from an X-ray tube to a subject and detects X-rays transmitted through the subject by using a multi-row detector having a plurality of X-ray detection rows arranged side by side along the slice direction (body axis direction), the acquired projection data are multiplied by the weights W1 and W2 before the execution of cone beam reconstruction processing of performing back projection along actual rays in consideration of the spread angle of X-rays in the slice direction, i.e., the cone angle of X-rays, as shown in FIG. 2B. Each of the projection data multiplied by the weights W1 and W2 is separately reconstructed (cone-beam reconstruction), and the generated images are added.

Figure 8:
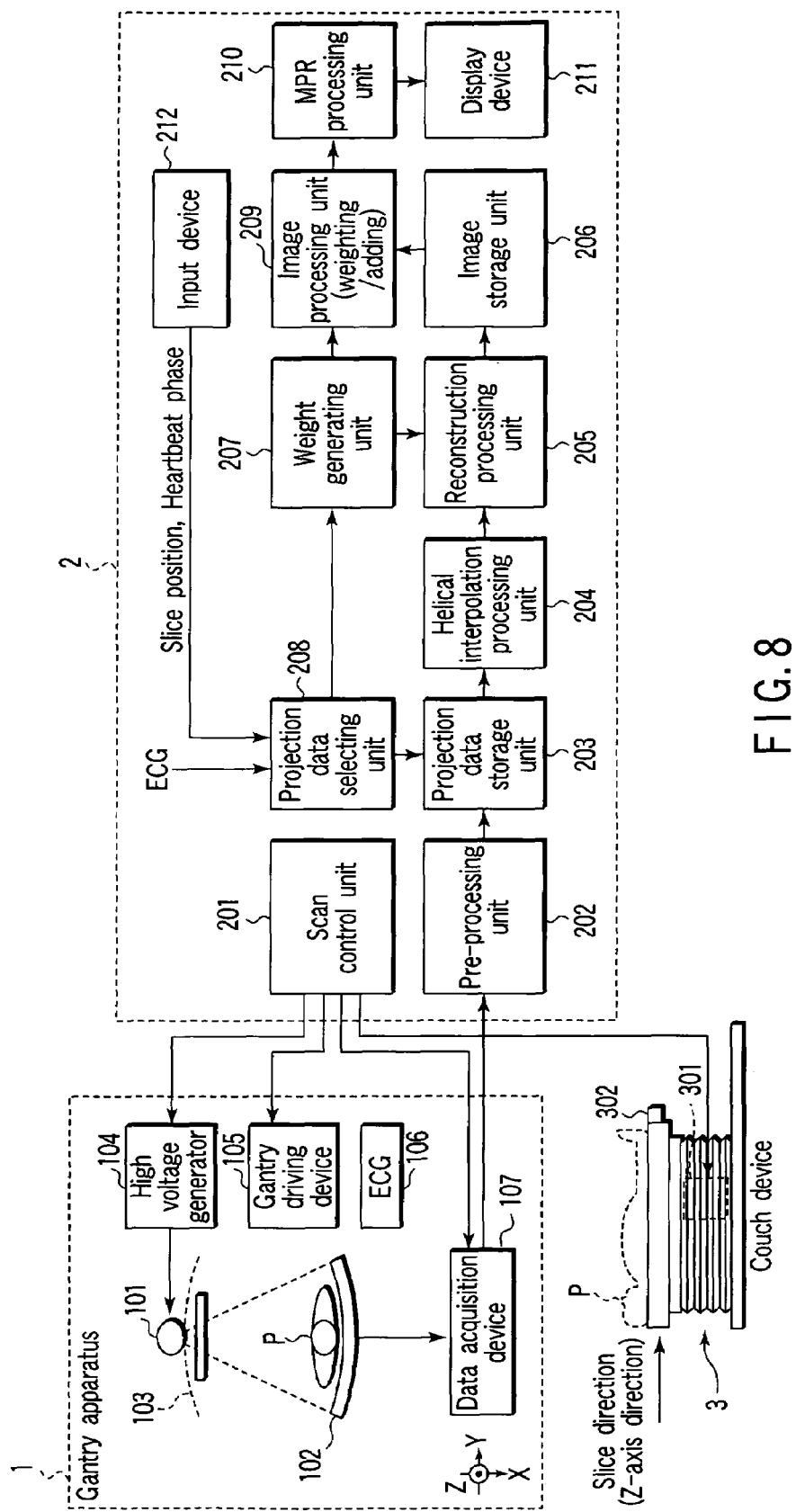
FIG. 8 is a block diagram showing another arrangement of the X-ray computed tomographic apparatus according to the embodiment of the present invention.
Figure 9:
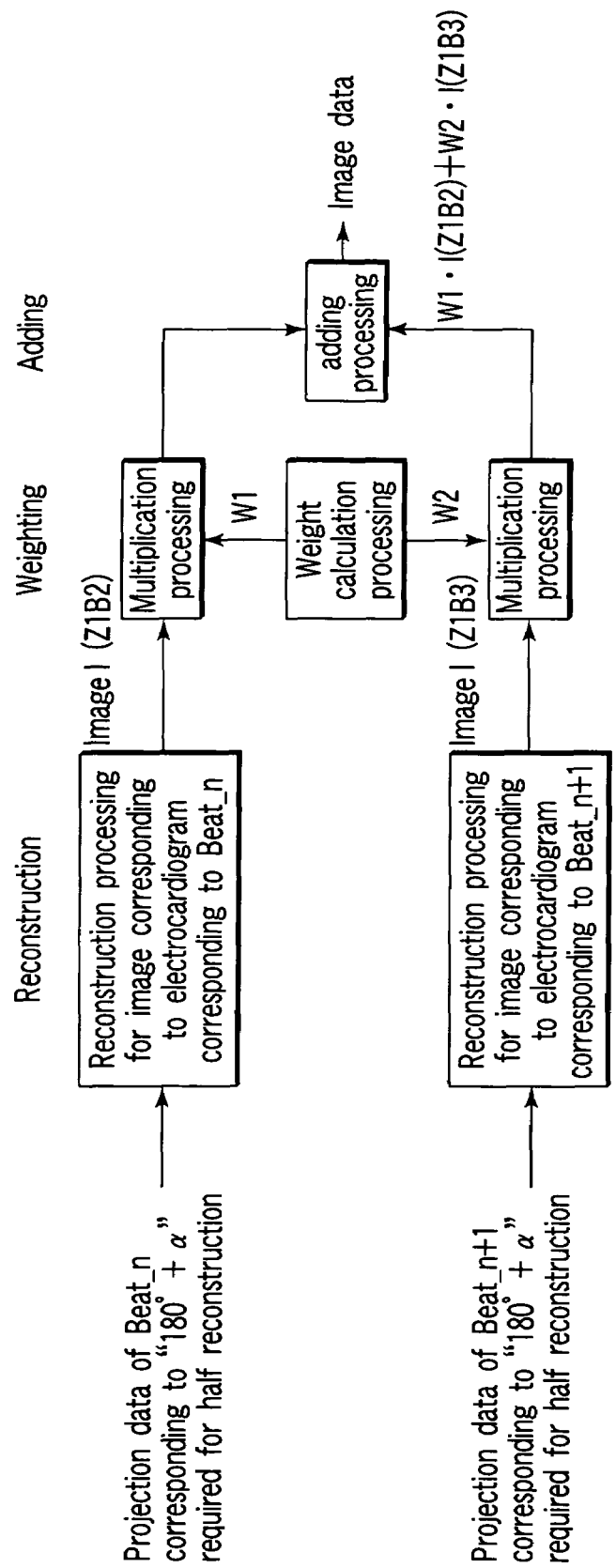
FIG. 9 is a view showing an outline of the flow of image reconstruction processing for one slice corresponding to an example of the arrangement in FIG. 8.
Figure 10:
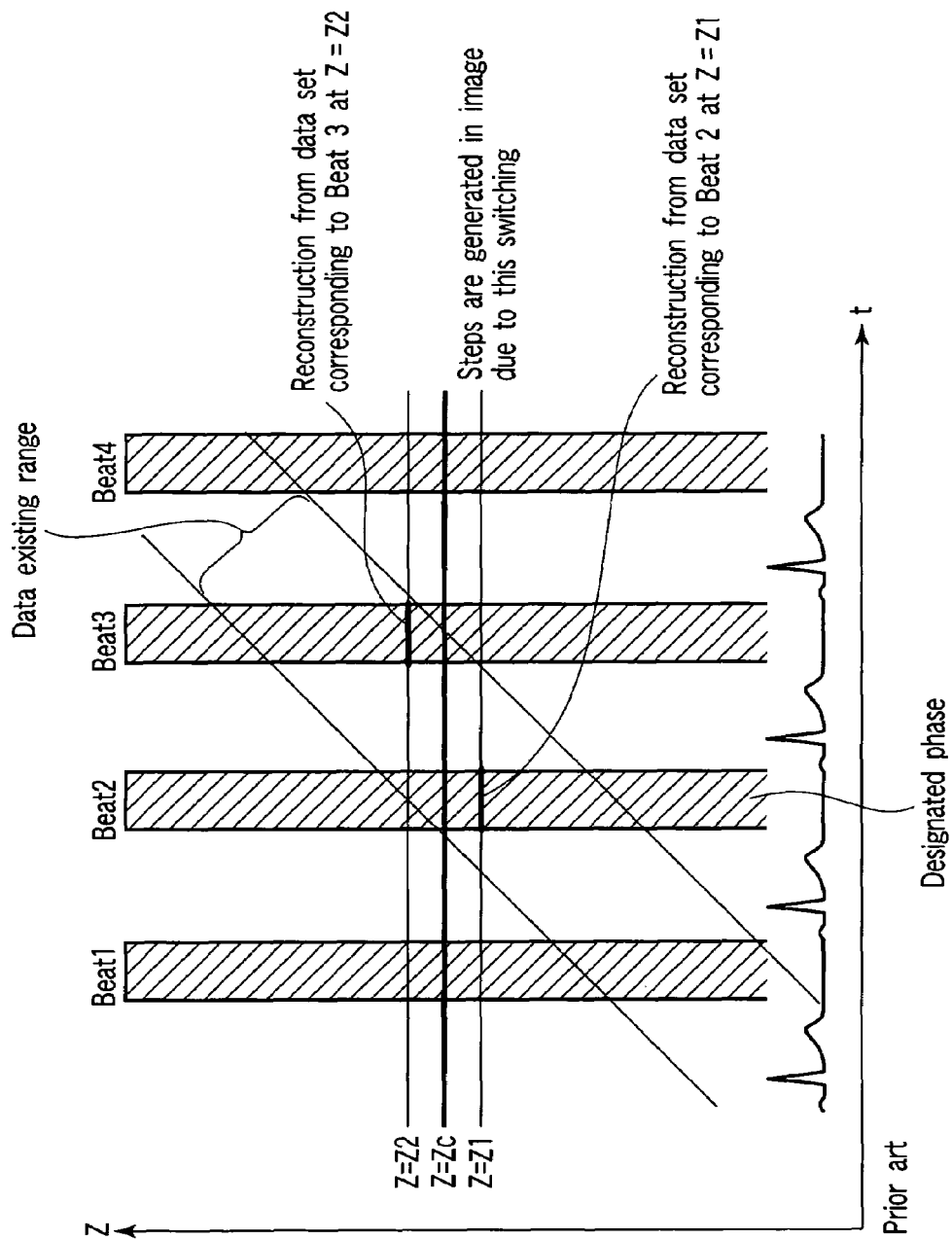
FIG. 10 is a graph for supplementarily explaining a conventional half ECG-gated reconstruction method.

According to the above description, raw data or projection data in different heartbeat periods are weighted/added before the execution of reconstruction. However, as shown in FIGS. 8 and 9, the image reconstruction processing unit 206 may reconstruct a plurality of tomographic images I(Z1B2) and I(Z1B3) concerning the same slice Z1 in different heartbeat periods before the execution of weighting/adding processing, and an image processing unit 213 may perform weighting/adding processing for the plurality of reconstructed tomographic images I(Z1B2) and I(Z1B3) by using the weights W1 and W2 generated by the weight generating unit 207.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An X-ray computed tomographic apparatus comprising:
   a gantry unit, which includes a detector with a plurality of X-ray detection element rows along a slice direction and an X-ray tube, and acquires projection data from a subject by helical scanning;
   an extraction unit which extracts a first projection data set corresponding to a first heartbeat period or a first respiratory period of the subject, and a second projection data set corresponding to a second heartbeat period or a second respiratory period of the subject from the acquired projection data, each of the first projection data set and the second projection data set covering an angle range required for reconstruction of one frame of an image;
   a weighting processing unit which weights each of the extracted first projection data set and the extracted second projection data set with a weight corresponding to a data acquisition position, wherein the weights depend on a center of a range in which the first projection data set and the second projection data set are prepared by interpolation from the projection data;
   a combining processing unit which combines the weighted first projection data and the weighted second projection data to generate a third data set; and
   a reconstruction processing unit which reconstructs an image data set on the basis of the generated third data set.

2. An X-ray computed tomographic apparatus comprising:
   a gantry unit, which includes a detector with a plurality of X-ray detection element rows along a slice direction and an X-ray tube, and acquires projection data from a subject by helical scanning;
   an extraction unit which extracts a first projection data set corresponding to a first heartbeat period or a first respiratory period of the subject, and a second projection data set corresponding to a second heartbeat period or a second respiratory period of the subject from the acquired projection data, each of the first projection data set and the second projection data set covering an angle range required for reconstruction of one frame of image;
   a weighting processing unit which weights each of the extracted first projection data set and the extracted second projection data set with a weight corresponding to a data acquisition position, wherein the weights depend on a center of a range in which the first projection data set and the second projection data set are prepared by interpolation from the projection data;
   a reconstruction processing unit which reconstructs a first image data set and a second image data set on the basis of the weighted first projection data set and the weighted second projection data set; and
   a combining processing unit which generates a third image data set by combining the reconstructed first image set and the reconstructed second image data set.

3. An X-ray computed tomographic apparatus comprising:
   a gantry unit, which includes a detector with a plurality of X-ray detection element rows along a slice direction and an X-ray tube, and acquires projection data from a subject by helical scanning;
   an extraction unit which extracts a first projection data set corresponding to a first heartbeat period or a first respiratory period of the subject, and a second projection data set corresponding to a second heartbeat period or a second respiratory period of the subject from the acquired projection data, each of the first projection data set and the second projection data set covering an angle range required for reconstruction of a 1-frame image;
   a reconstruction processing unit which reconstructs a first image data set and a second image data set on the basis of the extracted first projection data set and the extracted second projection data set;
   a weighting processing unit which weights each of the reconstructed first image data set and the reconstructed second image data set with a weight corresponding to a data acquisition position, wherein the weights depend on a center of a range in which the first projection data set and the second projection data set are prepared by interpolation from the projection data; and
   a combining processing unit which generates third image data by combining the weighted first image data set and the weighted second image data set.

4. An X-ray computed tomographic apparatus comprising:
   a gantry unit, which includes a detector with a plurality of X-ray detection element rows along a slice direction and an X-ray tube, and acquires projection data from a subject by helical scanning;
   an extraction unit which extracts a plurality of projection data sets in different heartbeat periods or respiratory periods of the subject from the acquired projection data, each of the projection data sets covering an angle range required for reconstruction of a 1-frame image; and
   a reconstruction processing unit which reconstructs a 1-frame image data set possessing a weight corresponding to a data acquisition position of each of the projection data sets on the basis of said plurality of extracted projection data sets,
   wherein the weights depend on a center of a range in which the plurality of projection data sets are prepared by interpolation from the projection data.

5. An apparatus according to claim 1, further comprising an interpolation processing unit which generates each of the first projection data set and the second projection data set by helical interpolation.

6. An apparatus according to claim 1, wherein, with a change in data acquisition position concerning a slice direction, a weight for the first projection data gradually decreases and a weight for the second projection data gradually increases.

7. An apparatus according to claim 1, wherein each of the first projection data set and the second projection data set covers an angle range of 180°+ fan angle.

8. An apparatus according to claim 7, wherein the weight has a value corresponding to a distance from the center of the range in which the first projection data set and the second projection data set are prepared from the projection data by interpolation to a center of each of the first data set and the second data set.

9. An apparatus according to claim 7, wherein the weight has a higher value as a center of each of the first projection data set and the second projection data set approaches the center of the range in which the first projection data set and the second projection data set are prepared from the projection data by interpolation.

10. An apparatus according to claim 7, wherein the weight has a lower value as a center of each of the first projection data set and the second projection data set separates from the center of the range in which the first projection data set and the second projection data set are prepared from the projection data by interpolation.

11. An apparatus according to claim 7, wherein the weight linearly decreases from the center of the range in which the first projection data set and the second projection data set can be prepared from the projection data by interpolation to an end of the range.

12. An apparatus according to claim 7, wherein the weight decreases curvilinearly from the center of the range in which the first projection data set and the second projection data set are prepared from the projection data by interpolation to an end of the range.

13. An apparatus according to claim 7, wherein the weight approximately changes trapezoidally from the center of the range in which the first projection data set and the second projection data set are prepared from the projection data by interpolation to an end of the range.

14. An apparatus according to claim 1, further comprising an image processing unit which generates an image data set of an arbitrary cross section from a plurality of image data sets at different slice positions which are reconstructed by the reconstruction processing unit by multi planar reformatting processing.

15. An image processing apparatus comprising:
an extraction unit which extracts a first projection data set corresponding to a first heartbeat period or a first respiratory period of a subject and a second projection data set corresponding to a second heartbeat period and a respiratory period of the subject from projection data acquired from the subject by helical scanning, each of the first projection data set and the second projection data set covering an angle range required for reconstruction of a 1-frame image;
a weighting processing unit which weights each of the extracted first projection data set and the extracted second projection data set with a weight corresponding to a data acquisition position, wherein the weights depend on a center of a range in which the first projection data set and the second projection data set are prepared by interpolation from the projection data;
a combining processing unit which generate a third data set by combining the weighted first projection data set and the weighted second projection data set; and
a reconstruction processing unit which reconstructs a 1-frame image data set on the basis of the generated third data set.

16. An image processing apparatus comprising:
an extraction unit which extracts a first projection data set corresponding to a first heartbeat period or a first respiratory period of a subject and a second projection data set corresponding to a second heartbeat period and a respiratory period of the subject from projection data acquired from the subject by helical scanning, each of the first projection data set and the second projection data set covering an angle range required for reconstruction of a 1-frame image;
a weighting processing unit which weights each of the extracted first projection data set and the extracted second projection data set with a weight corresponding to a data acquisition position, wherein the weights depend on a center of a range in which the first projection data set and the second projection data set are prepared by interpolation from the projection data;
a reconstruction processing unit which reconstructs a first image data set and a second image data set on the basis of the weighted first projection data set and the weighted second projection data set; and
a combining processing unit which generates a third image data set by combining the reconstructed first image data set and the reconstructed second image data set.

17. An image processing apparatus comprising:
an extraction unit which extracts a first projection data set corresponding to a first heartbeat period or a first respiratory period of a subject and a second projection data set corresponding to a second heartbeat period and a respiratory period of the subject from projection data acquired from the subject by helical scanning, each of the first projection data set and the second projection data set covering an angle range required for reconstruction of a 1-frame image;
a reconstruction processing unit which reconstructs a first image data set and a second image data set on the basis of the extracted first projection data set and the extracted second projection data set;
a weighting processing unit which weights each of the reconstructed first image data set and the reconstructed second image data set with a weight corresponding to a data acquisition position, wherein the weights depend on a center of a range in which the first projection data set and the second projection data set are prepared by interpolation from the projection data; and
a combining processing unit which generates third image data by combining the weighted first image data set and the weighted second image data set.

18. An image processing apparatus comprising:
an extraction unit which extracts a plurality of projection data sets in different heartbeat periods or respiratory periods of a subject from projection data acquired from the subject by helical scanning, each of the projection data sets covering an angle range required to reconstruct a 1-frame image; and
a reconstruction processing unit which reconstructs a 1-frame image data set possessing a weight corresponding to a data acquisition position of each of the projection data sets on the basis of said plurality of extracted projection data sets, wherein the weights depend on a center of a range in which the plurality of projection data sets are prepared by interpolation from the projection data.

* * * * *